(12) United States Patent
Crawford et al.

(10) Patent No.: US 7,507,522 B2
(45) Date of Patent: Mar. 24, 2009

(54) PHOTORESISTS COMPRISING POLYMERS DERIVED FROM FLUOROALCOHOL-SUBSTITUTED POLYCYCLIC MONOMERS

(75) Inventors: Michael Karl Crawford, Glen Mills, PA (US); Hoang Vi Tran, Wilmington, DE (US); Frank Leonard Schadt, III, Wilmington, DE (US); Fredrick Claus Zumsteg, Jr., Wilmington, DE (US); Andrew Edward Feiring, Wilmington, DE (US); Michael Fryd, Philadelphia, PA (US)

(73) Assignee: E. I. DuPont de Nemours and Company, Wilmington, DE (US)

( * ) Notice: Subject to any disclaimer, the term of this patent is extended or adjusted under 35 U.S.C. 154(b) by 255 days.

(21) Appl. No.: 11/578,278

(22) PCT Filed: May 17, 2005

(86) PCT No.: PCT/US2005/017325
§ 371 (c)(1),
(2), (4) Date: Oct. 11, 2006

(87) PCT Pub. No.: WO2005/118656
PCT Pub. Date: Dec. 15, 2005

(65) Prior Publication Data
US 2007/0207413 A1    Sep. 6, 2007

(51) Int. Cl.
*G03F 7/004* (2006.01)
(52) U.S. Cl. .................... 430/270.1; 430/905; 430/907; 526/281; 568/591
(58) Field of Classification Search ............. 430/270.1, 430/905, 907; 526/281; 568/591
See application file for complete search history.

(56) References Cited

U.S. PATENT DOCUMENTS

| | | | |
|---|---|---|---|
| 5,569,730 A | 10/1996 | Goodall et al. | |
| 6,653,419 B1 | 11/2003 | Petrov et al. | |
| 6,790,579 B1 * | 9/2004 | Goodall et al. | 430/170 |
| 6,875,555 B1 * | 4/2005 | Feiring et al. | 430/270.1 |
| 7,232,639 B2 * | 6/2007 | Maeda et al. | 430/270.1 |
| 7,422,836 B2 * | 9/2008 | Rhodes et al. | 430/270.1 |
| 2003/0025021 A1 | 2/2003 | Hiraguchi et al. | |
| 2003/0025022 A1 | 2/2003 | Wilcox et al. | |
| 2004/0219452 A1 * | 11/2004 | Rhodes et al. | 430/270.1 |

FOREIGN PATENT DOCUMENTS

| | | |
|---|---|---|
| JP | 2001-59172 | 3/2001 |
| WO | WO 97/33198 A1 | 9/1997 |
| WO | WO 00/67072 A1 | 11/2000 |

OTHER PUBLICATIONS

A. Sen, Organometallic Chemistry of Electrophilic Transition and Lanthanide Metal Ions. The Dominant Pathways for Reactions Involving C=C, C—C, and C—H Bonds. Acc. Chem. Res., 1988, vol. 21:421-428.

B.C. Trinque et. al., Advances in Resists for 157nm Microlithography, Proceedings of SPIE—The International Society for Optical Engineering, 2002, vol. 4690:58-68.

E. Reichmanis et. al., The Effect of Substituents on the Photosensitivity of 2-Nitrobenzyl Ester Deep UV Resists, J. Electrochem. Soc., 1983, vol. 130:1433-1437.

* cited by examiner

*Primary Examiner*—John S Chu

(57) ABSTRACT

The present invention relates to novel unsaturated polycyclic compounds containing two fluoroalcohol substitutents. This invention also relates to homopolymers and copolymers derived from such unsaturated polycyclic compounds. The copolymers are useful for photoimaging compositions and, in particular, photoresist compositions (positive-working and/or negative-working) for imaging in the production of semiconductor devices. The polymers are especially useful in photoresist compositions having high UV transparency (particularly at short wavelengths, e.g., 157 nm) which are useful as base resins in resists and potentially in many other applications.

18 Claims, 1 Drawing Sheet

PHOTORESISTS COMPRISING POLYMERS DERIVED FROM FLUOROALCOHOL-SUBSTITUTED POLYCYCLIC MONOMERS

FIELD OF THE INVENTION

The present invention relates to novel unsaturated polycyclic compounds containing two fluoroalcohol substitutents. This invention also relates to homopolymers and copolymers derived from such unsaturated polycyclic compounds. The copolymers are useful for photoimaging compositions and, in particular, photoresist compositions (positive-working and/or negative-working) for imaging in the production of semiconductor devices. The polymers are especially useful in photoresist compositions having high UV transparency (particularly at short wavelengths, e.g., 157 nm) which are useful as base resins in resists and potentially in many other applications.

BACKGROUND

Japanese Patent Application 2001-59172 discloses compounds having the structure:

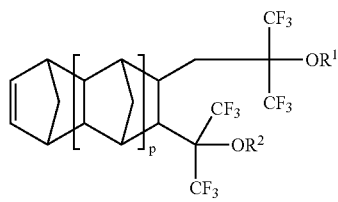

wherein $R^1$ and $R^2$ are hydrogens or monovalent organic groups and p is an integer of 0 to 5. The compounds are stated to be useful as polymer, functional material, pesticide or other starting material.

Polymers and photoresists derived from substituted norbornenes and from substituted TCNs (tricyclononanes) are disclosed in WO-00/67072, PCT/US03/25021 and PCT/US03/25022.

There is a critical need for novel resist compositions for use at 193 nm or lower wavelengths, and particularly at 157 nm, that have not only high transparency at short wavelengths but also other key properties, including good plasma etch resistance and adhesive properties.

SUMMARY OF THE INVENTION

In one embodiment, the invention provides a composition represented by Structure I

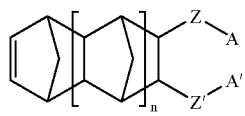

wherein n is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Z and Z' are each —$OCH_2$—, or Z-A and Z'-A' taken together are

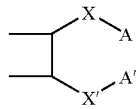

and X and X' are independently a direct bond, or a divalent group.

In another embodiment, the invention provides a homopolymer or copolymer comprising a repeat unit derived from an unsaturated polycyclic compound represented by Structure II:

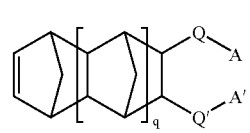

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;
Q and Q' are each a divalent group, a direct bond or Q-A and Q'-A' taken together are

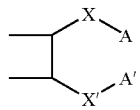

and X and X' are independently a direct bond, or a divalent group.

In another embodiment, the invention provides a photoresist comprising:

a. a homopolymer or copolymer comprising a repeat unit derived from an unsaturated polycyclic compound represented by Structure II:

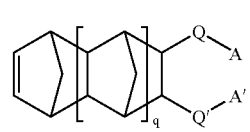

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Q and Q' are each a divalent group, a direct bond or Q-A and Q'-A' taken together are

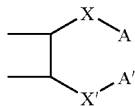

and X and X' are independently a direct bond, or a divalent group; and b. a photoactive component.

In another embodiment, the invention provides a photoresist-coated substrate comprising;

a. a substrate; and b. a photoresist comprising:

1. a homopolymer or copolymer comprising a repeat unit derived from an unsaturated polycyclic compound represented by Structure II:

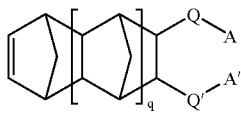

(II)

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;
Q and Q' are each a divalent group, a direct bond or Q-A and Q'-A' taken together are

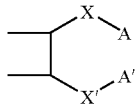

and X and X' are independently a direct bond, or a divalent group; and 2. a photoactive component.

BRIEF DESCRIPTION OF THE FIGURE

The Figure shows a graph of dissolution rate vs. percentage of NB-di-F—OH in a TFE/NB—F—OH/NB-di-F—OH terpolymer.

DETAILED DESCRIPTION OF THE INVENTION

Unsaturated Polycyclic Compounds

Figure 1:
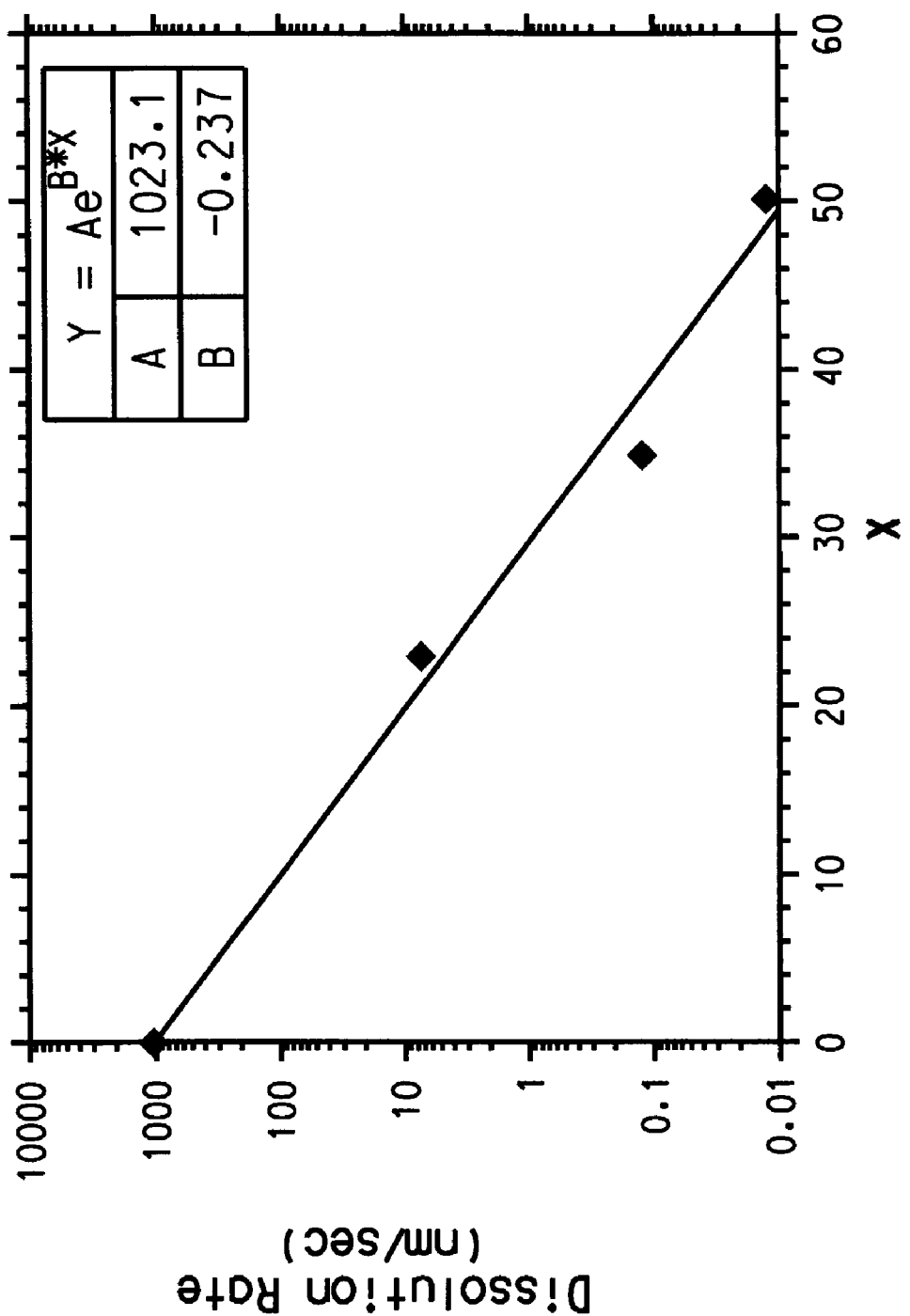

One embodiment of this invention provides a composition represented by Structure I

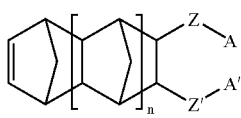

(I)

wherein n is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Z and Z' are each —$OCH_2$—, or Z-A and Z'-A' taken together are

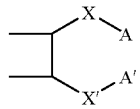

and X and X' are independently a direct bond, or a divalent group.

In one specific embodiment, the polycyclic compound is a norbornene (n=0), in which Z=Z'=—$OCH_2$—, $R_f$=$R_f'$=$CF_3$ and $R^1$=H. In another specific embodiment, the polycyclic compound is a TCN derivative, in which Z-A and Z'-A' taken together are

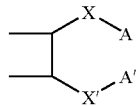

and X and X' are —$CH_2OCH_2$—.

Some illustrative, but nonlimiting, examples of representative monomers of Structures (I) that are within the scope of the invention are presented below:

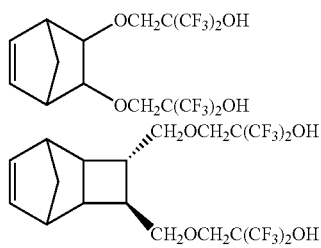

Preparation of these fluoroalcohol-substituted, unsaturated polycyclic compounds can be achieved by reaction of the corresponding diols with a fluorinated epoxide. Methods of synthesizing the fluorinated epoxides are disclosed in U.S. Pat. No. 6,653,419.

Homopolymers

Homopolymers comprising repeat units derived from a composition of Structure II can be prepared by metal catalyzed addition polymerization, where Structure II is represented by

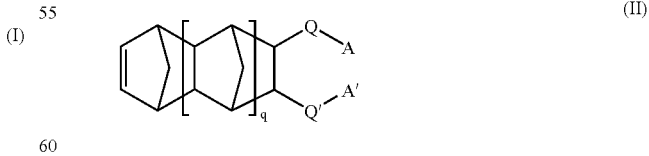

(II)

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Q and Q' are each a divalent group, a direct bond or Q-A and Q'-A' taken together are

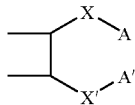

and X and X' are independently a direct bond, or a divalent group.

Transition metal catalysts for vinyl-addition polymerization of functionalized norbornenes are generally based on Pd(II) and Ni(II). For example, $[Pd(MeCN)_4](BF_4)_2$ will catalyze norbornene polymerization (Sen, A. *Acc. Chem. Res.* 1988, 21, 421). Ni catalysts, e.g., $Ni(toluene)(C_6F_5)_2$, can also polymerize functionalized norbornenes. Molecular weight in Ni-catalyzed polymerizations can be controlled using alpha-olefins as chain-transfer agents [U.S. Pat. No. 5,569,730; WO 97/33198]. Vinyl addition polymerization of norbornene fluoroalcohol monomers has been demonstrated using palladium catalysts. The resulting polymers are useful as 157 and 193 nm photoresist binders [PCT WO 00/67072; B. C. Trinque, et al., Proceedings of SPIE—The International Society for Optical Engineering (2002), 4690 (Pt. 1, Advances in Resist Technology and Processing XIX), 58-68.]

Suitable metal catalysts for the preparation of the homopolymers of this invention include $[Pd(MeCN)_4](BF_4)_2$ and $Ni(toluene)(C_6F_5)_2$.

Copolymers

One embodiment of this invention includes copolymers comprising repeat units derived from one or more unsaturated polycyclic compositions of Structure II, optionally further comprising one or more other polymerizable monomers. Suitable polymerizable monomers include other polycyclic unsaturated compounds, ethylene, alpha-olefins, 1,1'-disubstituted olefins, vinyl esters, vinyl ethers, 1,3-dienes, fluoroolefins, acrylates, methacrylates, and styrenes.

Copolymers of this invention can be prepared, for example, by radical initiated polymerization. Suitable radical initiators include peroxydicarbonates, such as bis(tert-butylcyclohexyl)peroxydicarbonate, and azo compounds, such as 2,2'-azo-bis-isobutyronitrile.

Some illustrative, but nonlimiting, examples of representative monomers of Structure (II) that are within the scope of the invention are presented below:

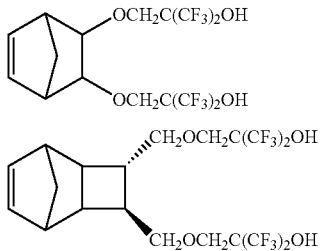

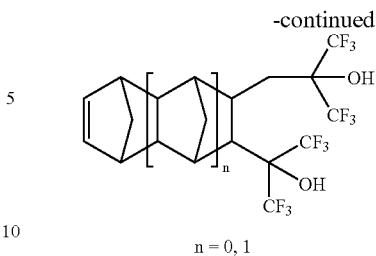

n = 0, 1

Representative fluoroolefins for use in making copolymers of this invention include, but are not limited to, tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene-4-methyl-1,3-dioxolane), $CF_2=CFO(CF_2)_tCF=CF_2$, where t is 1 or 2, and $R_f''OCF=CF_2$ wherein $R_f''$ is a saturated fluoroalkyl group of from 1 to 10 carbon atoms. A preferred comonomer is tetrafluoroethylene.

The homopolymers and copolymers of this invention inherently comprise fluoroalcohol or protected fluoroalcohol groups introduced via the repeat units derived from compositions represented by Structure II. In addition, the copolymers of this invention can further comprise one or more substituted polymerizable monomers, wherein at least one substitutent on the polymerizable monomer is a fluoroalcohol group having the structure:

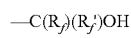

wherein $R^f$ and $R_f'$ are the same or different fluoroalkyl groups of from 1 to 10 carbon atoms or taken together are $(CF_2)_m$ wherein m is 2 to 10. The phrase "taken together" indicates that $R_f$ and $R_f'$ are not separate, discrete fluorinated alkyl groups, but that together they form a ring structure such as is illustrated below for a 5-membered ring:

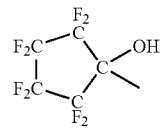

$R_f$ and $R_f'$ can be partially fluorinated alkyl groups without limit according to the invention except that there must be a sufficient degree of fluorination present to impart acidity to the hydroxyl (—OH) of the fluoroalcohol functional group, such that the hydroxyl proton is substantially removed in basic media, such as in aqueous sodium hydroxide solution or tetraalkylammonium hydroxide solution. In preferred embodiments according to the invention, there will be sufficient fluorine substitution present in the fluorinated alkyl groups of the fluoroalcohol functional group such that the hydroxyl group will have a pKa value of 5<pKa<11. Preferably, $R_f$ and $R_f'$ are independently perfluoroalkyl groups of 1 to 5 carbon atoms, and, most preferably, $R_f$ and $R_f'$ are both trifluoromethyl ($CF_3$).

The fluorinated polymers of this invention can further comprise a repeat unit derived from a polymerizable monomer containing a fluoroalcohol functional group having the structure:

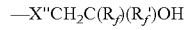

wherein $R_f$ and $R_f'$ are the same or different fluoroalkyl groups of from 1 to 10 carbon atoms or taken together are $(CF_2)_m$ wherein m is 2 to 10, X" is oxygen, sulfur, nitrogen or phosphorous. Preferably, X"=O (i.e., a divalent oxygen group).

Some illustrative, but nonlimiting, examples of representative comonomers containing a fluoroalcohol functional group that are within the scope of the invention are presented below:

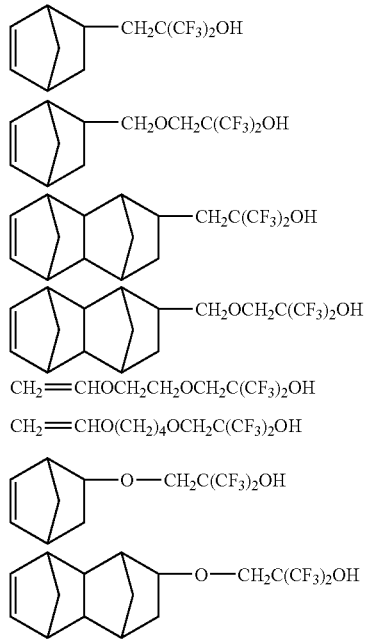

The copolymer can further comprise at least one acid-containing or protected acid-containing monomer of structural unit:

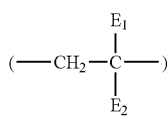

wherein $E_1$ is H or $C_1$-$C_{12}$ alkyl; $E_2$ is $CO_2E_3$, $SO_3E$, or other acidic group; and E and $E_3$ are independently selected from the group of H, unsubstituted $C_1$-$C_{12}$ alkyl, and heteroatom substituted $C_1$-$C_{12}$ alkyl. Suitable heteroatoms are oxygen, nitrogen, sulfur, halogen and phosphorus atoms. When the heteroatom is oxygen, the substituent may be a hydroxyl group, such as in 2-hydroxyethylacrylate, or an ether group, such as in 2-methoxyethyl acrylate. When the heteroatom is N, the substituent may be a cyano group, such as in 2-cyanoethyl acrylate. Alkyl groups can contain 1 to 12 carbon atoms and preferably 1 to 8 carbon atoms. A preferred acid-containing binder polymer for aqueous processability (aqueous development) is a carboxylic acid-containing copolymer. The level of carboxylic acid groups is determined for a given composition by optimizing the amount needed for good development in aqueous alkaline developer. The additional monomers can be acrylates. Tertiary alkyl acrylates such as tert-butyl acrylate, 2-methyl-2-adamantyl acrylate and 2-methyl-2-norbornyl acrylate can provide acid-sensitive functionality for image formation as discussed above. Other acrylates, such as acrylic acid, methyl acrylate, ethyl acrylate, propyl acrylate, 2-hydroxyethyl acrylate, 2-methoxyethyl acrylate, 2-cyanoethyl acrylate, glycidyl acrylate and 2,2,2-trifluoroethyl acrylate can be employed to modify the adhesion or solubility of the polymer. In one embodiment tert-butylacrylate can be incorporated into the polymer to provide acid-labile tert-butyl ester groups.

Polar monomers such as vinyl acetate can also be incorporated into the copolymer in order to assist aqueous development or otherwise modify polymer properties.

The fluoro alcohol group and/or other acid group of the polymer can contain a protecting group that protects the fluorinated alcohol group and/or other acid group (i.e., the protected group) from exhibiting its acidity while in this protected form. As one illustrative example, the tertiary-butyl group is the protecting group in a tertiary-butyl ester and this protecting group protects the free acid. In undergoing deprotection (conversion of protected acid to free acid), the ester is converted to the corresponding acid.

An alpha-alkoxyalkyl ether group is a preferred protecting group for the fluoroalcohol group in order to maintain a high degree of transparency in the photoresist composition. The resulting protected fluoroalcohol group has the structure:

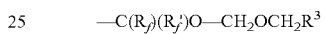

In this protected fluoroalcohol, $R_f$ and $R_f'$ are the same or different fluoroalkyl groups of from 1 to 10 carbon atoms or taken together are $(CF_2)_m$ wherein m is 2 to 10; $R^3$ is hydrogen or a linear or branched alkyl group of 1 to 10 carbon atoms. An illustrative, but non-limiting, example of an alpha-alkoxyalkyl ether group that is effective as a protecting group in a protected acid group, is methoxy methyl ether (MOM). A protected fluoroalcohol with this particular protecting group can be obtained by reaction of chloromethylmethyl ether with the fluoroalcohol.

The fluoroalcohol functional group (protected or unprotected) of this invention can be used alone or it can be used in combination with one or more other acid groups, such as a carboxylic acid functional group (unprotected) or the t-butyl ester of a carboxylic acid functional group (protected).

In this invention, often, but not always, the components having protected groups are repeat units having protected acid groups that have been incorporated in the base copolymer resins of the compositions. Frequently, the protected acid groups are present in one or more comonomer(s) that are polymerized to form the copolymer of this invention. Alternatively, in this invention, a copolymer can be formed by copolymerization with an acid-containing comonomer and then subsequently acid functionality in the resulting acid-containing copolymer can be partially or wholly converted by appropriate means to derivatives having protected acid groups.

Photoresist Development

Protective Groups for Removal by PAC Catalysis

Photoactive Component (PAC)

The photoresist compositions of this invention can contain at least one photoactive component (PAC) that can produce either acid or base upon exposure to actinic radiation during the development process. If an acid is produced upon exposure to actinic radiation, the PAC is termed a photoacid generator (PAG). If a base is produced upon exposure to actinic radiation, the PAC is termed a photobase generator (PBG).

Suitable photoacid generators for this invention include, but are not limited to, 1) sulfonium salts (structure III), 2)

iodonium salts (structure IV), and 3) hydroxamic acid esters, such as structure V.

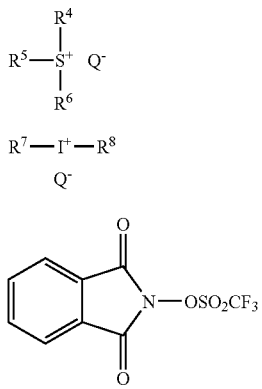

In structures III to IV, $R^4$ to $R^8$ are, independently, substituted or unsubstituted $C_6$ to $C_{20}$ aryl, or substituted or unsubstituted $C_7$-$C_{40}$ alkylaryl or aralkyl. Representative aryl groups include, but are not limited to, phenyl, naphthyl, and anthracenyl. Suitable heteroatom substituents include, but are not limited to, one or more oxygen, nitrogen, halogen or sulfur atoms. When the heteroatom is oxygen, the substituent can contain hydroxyl (—OH) or $C_1$-$C_{20}$ alkyloxy (e.g., $C_{10}H_{21}O$). The anion $Q^-$ in structures III-IV can be, but is not limited to, $SbF_6$-(hexafluoroantimonate), $CF_3SO_3$— (trifluoromethylsulfonate=triflate), and $C_4F_9SO_3$— (perfluorobutylsulfonate).

Functionality for Development

For use in a photoresist composition, the fluorine-containing copolymer should contain sufficient functionality to render the photoresist developable so as to produce a relief image, following imagewise exposure to ultraviolet radiation having wavelength of ≦366 nm. In some preferred embodiments, the sufficient functionality is selected from an acid and/or a protected acid group, as described above. Such acid or protected acid groups have been found to render the exposed portions of photoresist soluble in basic solution upon exposure to sufficient ultraviolet radiation having a wavelength of ≦366 nm, while the unexposed portions are insoluble in the basic solution.

For development, one or more groups within the fluorine-containing copolymers should contain one or more components having protected acid groups that can yield, by catalysis of acids or bases generated photolytically from the photoactive compound (PAC), hydrophilic acid or base groups.

A given protected acid group is one that is normally chosen on the basis of its being acid labile, such that when photoacid is produced upon imagewise exposure, the acid will catalyze deprotection of the protected acid group and production of hydrophilic acid groups that are necessary for development under aqueous conditions. In addition, the fluorine-containing copolymers can also contain acid functionality that is not protected.

Examples of basic developer include, but are not limited to, sodium hydroxide, potassium hydroxide, and ammonium hydroxide solutions. Typically, a basic developer is an aqueous alkaline liquid such as a wholly aqueous solution containing 0.262 N tetramethylammonium hydroxide (with development at 25° C. usually for ≦120 seconds) or 1% sodium carbonate by weight (with development at a temperature of 30° C. usually ≦2 minutes).

When an aqueous processable photoresist is coated or otherwise applied to a substrate and imagewise exposed to UV light, development of the photoresist composition can require that the binder material contains sufficient acid groups (e.g., carboxylic acid groups) and/or protected acid groups that are at least partially deprotected upon exposure to render the photoresist (or other photoimageable coating composition) processable in aqueous alkaline developer.

In one embodiment of the invention, the copolymer having one or more protected acid groups yields a carboxylic acid as the hydrophilic group upon exposure to photogenerated acid. Such protected acid groups include, but are not limited to, A) esters capable of forming, or rearranging to, a tertiary cation, B) esters of lactone, C) acetal esters, D) β-cyclic ketone esters, E) α-cyclic ether esters, and F) MEEMA (methoxy ethoxy ethyl methacrylate) and other esters which are easily hydrolyzable because of anchimeric assistance. Some specific examples in category A) are t-butyl ester, 2-methyl-2-adamantyl ester, and isobornyl ester.

A typical acidic group is the hexafluoroisopropanol group which can be incorporated by use of hexafluoroisopropanol group-containing monomers as illustrated by the examples. Some or all of the hexafluoroisopropanol groups can be protected as, for example, acid-labile alkoxymethyl ethers or tert-butylcarbonates.

Examples of components having protected acid groups that yield an alcohol as the hydrophilic group upon exposure to photogenerated acid or base include, but are not limited to, t-butoxycarbonyl (t-BOC), t-butyl ether, and 3-cyclohexenyl ether.

In the case of a negative-working photoresist layer, the photoresist layer will be removed during development in portions which are unexposed to UV radiation but will be substantially unaffected in exposed portions during development using either a supercritical fluid or an organic solvent.

Dissolution Inhibitors and Additives

Various dissolution inhibitors can be utilized in this invention. Ideally, dissolution inhibitors (DIs) for far and extreme UV resists (e.g., 193 nm resists) should be designed or chosen to satisfy multiple materials needs, including dissolution inhibition, plasma etch resistance, and adhesion behavior of resist compositions comprising a given DI additive. Some dissolution inhibiting compounds also serve as plasticizers in resist compositions.

A variety of bile-salt esters (i.e., cholate esters) are particularly useful as DIs in the compositions of this invention. Bile-salt esters are known to be effective dissolution inhibitors for deep UV resists, beginning with work by Reichmanis et al. in 1983. (E. Reichmanis et al., "The Effect of Substituents on the Photosensitivity of 2-Nitrobenzyl Ester Deep UV Resists", *J. Electrochem. Soc.* 1983, 130, 1433-1437.) Bile-salt esters are particularly attractive choices as DIs for several reasons, including their availability from natural sources, their high alicyclic carbon content, and particularly for their transparency in the deep and vacuum UV region of the electromagnetic. Furthermore, the bile-salt esters are also attractive DI choices since they may be designed to have a wide range of hydrophobic or hydrophilic compatibilities, depending upon hydroxyl substitution and functionalization.

Representative bile-acids and bile-acid derivatives that are suitable as additives and/or dissolution inhibitors for this invention include, but are not limited to, cholic acid, deoxycholic acid, lithocholic acid, t-butyl deoxycholate, t-butyl lithocholate, and t-butyl-3-α-acetyl lithocholate.

The invention is not limited to use of bile-acid esters and related compounds as dissolution inhibitors. Other types of dissolution inhibitors, such as various diazonaphthoquinones (DNQs) and diazocoumarins (DCs), can be utilized in this invention in some applications. Diazanaphthoquinones and diazocoumarins are generally suitable in resists compositions designed for imaging at higher wavelengths of UV light (e.g., 365 nm and perhaps at 248 nm). These dissolution inhibitors are generally not preferred in resist compositions designed for imaging with UV light at 193 nm or lower wavelengths, since these compounds absorb strongly in this region of the UV and are usually not sufficiently transparent for most applications at these low UV wavelengths.

Solvents:

Photoresists of this invention are prepared as coating compositions by dissolving the components of the photoresist in a suitable solvent, including: ether esters such as propyleneglycol monomethyl ether acetate, 2-ethoxyethyl acetate, 2-methoxyethyl acetate, and ethyl 3-ethoxypropionate; ketones such as cyclohexanone, 2-heptanone, and methyl ethyl ketone; esters such as butyl acetate, ethyl lactate, methyl lactate, and ethyl acetate; glycol ethers such as propylene glycol monomethyl ether, ethylene glycol monomethyl ether, ethyleneglycol monoethyl ether, and 2-methoxyethyl ether (diglyme); unsubstituted and substituted aromatic hydrocarbons such as toluene and chlorobenzene; and fluorinated solvents such as CFC-113 (1,1,2-trichlorotrifluoro-methane, E. I. DuPont de Nemours and Company) and 1,2-bis(1,1,2,2-tetrafluoroethoxy)ethane. A high boiling solvent can be added, including: an unsubstituted or substituted aromatic hydrocarbon, such as xylene; an ether such as benzyl ethyl ether or dihexyl ether; a glycol ether such as diethyleneglycol monomethyl ether or diethyleneglycol monoethyl ether; a ketone such as acetonylacetone or isophorone; an alcohol such as 1-octanol, 1-nonanol, or benzylalcohol; an ester such as benzyl acetate, ethyl benzoate, diethyl oxalate, diethyl maleate, ethylene carbonate, or propylene carbonate; or a lactone such as γ-butyrolactone or δ-valerolactone. Alternately, supercritical $CO_2$ may be useful as a solvent. These solvents can be used alone or in admixture of two or more. Typically, the solids content of the photoresist varies between 5 and 50% by weight of the total weight of the photoresist composition.

Other Components

The compositions of this invention can contain optional additional components. Examples of additional components which can be added include, but are not limited to, bases, surfactants, resolution enhancers, adhesion promoters, residue reducers, coating aids, plasticizers, and $T_g$ (glass transition temperature) modifiers.

Process Steps

For microlithography, a solution of the photoresist composition is applied to a suitable substrate such as a microelectronic wafer typically employed in the semiconductor industry. Examples include, but are not limited to, silicon and SiON wafers. The solvent is then removed by evaporation.

Imagewise Exposure

The photoresist compositions of this invention are sensitive in the ultraviolet region of the electromagnetic spectrum and especially to those wavelengths ≦366 nm. Imagewise exposure of the photoresist compositions of this invention can be done at many different UV wavelengths including, but not limited to, 365 nm, 248 nm, 193 nm, 157 nm, and lower wavelengths. Imagewise exposure is preferably done with ultraviolet light of 248 nm or lower wavelengths; more preferably with ultraviolet light of 193 nm or lower wavelengths; and still more preferably with ultraviolet light of 157 nm or lower wavelengths. Imagewise exposure can either be done digitally with a laser or equivalent device, or digitally or non-digitally with use of a photomask. Digital imaging with a laser is preferred. Suitable laser devices for digital imaging of the compositions of this invention include, but are not limited to, an argon-fluorine excimer laser with UV output at 193 nm, a krypton-fluorine excimer laser with UV output at 248 nm, and a fluorine (F2) laser with output at 157 nm. Since, as discussed supra, use of UV light of lower wavelength for imagewise exposure corresponds to higher resolution (lower resolution limit), the use of a lower wavelength (e.g., 193 nm or 157 nm or lower) is generally preferred over use of a higher wavelength (e.g., 248 nm or higher). Specifically, imaging at 157 nm is preferred over imaging at 193 nm for this reason.

The present photoresists are useful for 365 nm (I-line), 248 nm (KrF laser), and especially 193 nm (ArF laser) and 157 nm (F2 laser) microlithography. These photoresists are critical in allowing for the imaging of feature sizes in the submicrometer range.

Substrate

The substrate employed in this invention can be silicon, silicon oxide, silicon oxynitride, silicon nitride, or various other materials used in semiconductive manufacture. In a preferred embodiment, the substrate can be in the form of a microelectronic wafer. The microelectronic wafer can be prepared from silicon, silicon oxide, silicon oxynitride, and silicon nitride.

| GLOSSARY | |
|---|---|
| Analytical/Measurements | |
| bs | broad singlet |
| δ | NMR chemical shift measured in the indicated solvent |
| g | gram |
| NMR | Nuclear Magnetic Resonance |
| $^1$H NMR | Proton NMR |
| $^{13}$C NMR | Carbon-13 NMR |
| $^{19}$F NMR | Fluorine-19 NMR |
| s | singlet |
| sec. | second(s) |
| m | multiplet |
| mL | milliliter(s) |
| mm | millimeter(s) |
| $T_g$ | Glass Transition Temperature |

-continued

| GLOSSARY | |
|---|---|
| $M_n$ | Number-average molecular weight of a given polymer |
| $M_w$ | Weight-average molecular weight of a given polymer |
| $P = M_w/M_n$ | Polydispersity of a given polymer |
| Absorption coefficient | AC = A/b, where A, absorbance,= $Log_{10}(1/T)$ and b = film thickness in microns, where T = transmittance as defined below. |
| Transmittance | Transmittance, T, = ratio of the radiant power transmitted by a sample to the radiant power incident on the sample and is measured for a specified wavelength X (e.g., nm). |
| Chemicals/Monomers (Commercial source) | |
| Chemicals/Monomers | |
| t-BuAc | tert-Butyl acrylate (Aldrich Chemical Company, Milwaukee, WI) |
| GBLA | gamma-Butyrolactone acrylate (Idemitsu Chemical USA, Southfield, MI) |
| HAdA | Hydroxyadamantyl acrylate (2-Propenoic acid, 3-hydroxytricyclo[3.3.1.1 3,7]dec-1-yl ester) [CAS registry number 216581-76-9] (Idemitsu Chemical USA, Southfield, MI) |
| 2HEtA | 2-Hydroxyethyl acrylate (Aldrich Chemical Company, Milwaukee, WI) |
| HFIBO |  (E. I. DuPont de Nemours & Co, Wilmington, DE) |
| HFPO-dp | $[CF_3CF_2CF_2OCF(CF_3)CO_2]_2$ (E. I. DuPont de Nemours & Go, Wilmington, DE) |
| MAdA | 2-Methyl-2-adamantyl acrylate (2-propenoic acid, 2-methyltricyclo[3.3.1.13,7]dec-2-yl ester) [GAS Registry number 249562-06-9] (Idemitsu Ghemical USA, Southfield, MI) |
| NB-F-OH | 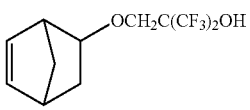 |
| NB-di-F-OH | 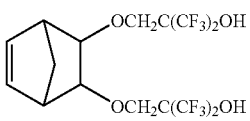 |
| Perkadox ® 16N | Bis(4-tert-butylcyclohexyl)peroxy-dicarbonate (Noury Chemical Corp., Burt, NY) |
| PinAc | 2-Propenoic acid, 2-hydroxy-1,1,2-trimethyipropyl ester [CAS Reg number 97325-36-5] |
| Solkane ® 365mfc | 1,1,1,3,3-Pentafluorobutane (Solvay Fluor, Hannover, Germany) |
| TCN-(CO2-t-Bu)(CO2-t-Bu) | 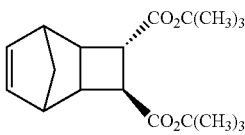 |

GLOSSARY

TCN-di-F-OH

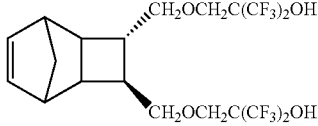

TCN-(F2)(F2)

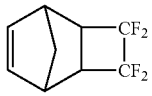

TFE — Tetrafluoroethylene, (E. I. DuPont de Nemours & Company, Wilmington, DE)

Ultraviolet

Extreme UV — Region of the electromagnetic spectrum in the ultraviolet that ranges from 10 nm to 200 nm Far UV — Region of the electromagnetic spectrum in the ultraviolet that ranges from 200 nm to 300 nm UV — Ultraviolet region of the electromagnetic spectrum which ranges from 10 nm to 390 nm Near UV — Region of the electromagnetic spectrum in the ultraviolet that ranges from 300 nm to 390 nm

EXAMPLES

Unless otherwise specified, all temperatures are in degrees Celsius, all mass measurements are in grams, and all percentages are weight percentages, except for polymer compositions, which are expressed as mole % of the constituent monomer repeat units.

Glass transition temperatures ($T_g$) were determined by DSC (differential scanning calorimetry) using a heating rate of 20° C./min. Data is reported from the second heat. The DSC unit used is a Model DSC2910 made by TA Instruments, Wilmington, Del.

Assessment of 157 nm imaging sensitivity can be done using a Lambda-Physik Compex 102 excimer laser configured for 157 nm operation. Vacuum ultraviolet transmission measurements are made using a McPherson spectrometer equipped with a $D_2$ light source. Samples are spin-coated at several thicknesses on $CaF_2$ substrates. The contribution of the substrate to the transmission is approximately removed by spectral division.

More specifically, all absorption coefficient measurements for polymers can be made using the procedure listed below.

1. Samples are first spin-coated on silicon wafers on a Brewer Cee (Rolla, Mo.), Spincoater/Hotplate model. 100CB.
   a) Two to four silicon wafers are spun at different speeds (e.g., 2000, 3000, 4000, 6000 rpm) to obtain differing film thickness and the coated wafers are subsequently baked at 120° C. for 30 min. The dried films are then measured for thickness on a Gaertner Scientific (Chicago, Ill.), L116A Ellipsometer (400 to 1200 angstrom range). Two spin speeds are then selected from this data to spin the $CaF_2$ substrates for the spectrometer measurement.
   b) Two $CaF_2$ substrates (1" dia.×0.80" thick) are selected and each is run as a reference data file on a McPherson Spectrometer (Chemsford, Mass.), 234/302 monochrometer, using a 632 Deuterium Source, 658 photomultiplier, and Keithley 485 picoammeter.
   c) Two speeds are selected from the silicon wafer data a) to spin the sample material onto the $CaF_2$ reference substrates (e.g., 2000 and 4000 rpm) to achieve the desired film thickness. Then each is baked at 120° C. for 30 min. and the sample spectra is collected on the McPherson Spectrometer; the sample files are then divided by the reference $CaF_2$ files.
   d) The resulting absorbance files are then adjusted (sample film on $CaF_2$ divided by $CaF_2$ blank) for film thickness to give absorbance per micron (abs/mic), which is done using GRAMS386 and KALEIDAGRAPH software.

The term "clearing dose" indicates the minimum exposure energy density (e.g., in units of $mJ/cm^2$) to enable a given photoresist film, following exposure, to undergo development.

Example 1

Synthesis of 2,3-Dihydroxynorborn-5-ene

A 1-L round bottom flask was charged under nitrogen with 450 mL of tert-butanol, 30 mL pyridine, 92 g (1 mol) of norbornadiene, 257.4 g of a 50% aqueous solution of 4-methylmorpholine-N-oxide (Sigma-Aldrich Chemical Company, Milwaukee, Wis.) and 6 mL of a 4% aqueous solution of osmium tetroxide (Sigma-Aldrich Chemical Company). This mixture was heated at reflux overnight. The solution was cooled to room temperature and treated with 3 g of sodium hydrosulfite and 30 g of Florisil. The pH of the solution was adjusted to 7 by addition of aqueous HCl. The mixture was stirred and filtered through Celite. The filtrate was concentrated on a rotary evaporator to remove most of the organic solvents. The remaining solution was acidified to pH 1-2 and extracted with ether. The ether extracts were washed with saturated aqueous sodium chloride solution, dried over anhydrous magnesium sulfate and concentrated to give 65.3 g (52%) of the desired product as a white solid judged sufficiently pure for subsequent transformation. Another sample prepared by the same procedure had $^1$H-NMR (ppm, CDCl$_3$, major isomer): δ 1.60 (1H, dp, J=9.5, 2.0 Hz), 1.87 (1H, d, J=9.0 Hz), 2.67 (2H, p, J=2.0 Hz), 3.68 (2H, d, J=2.0 Hz), 6.01 (2H, t, J=2.0 Hz). $^{13}$C—NMR (ppm, CDCl$_3$, major isomer): δ 42.4, 48.2, 69.1, 136.6. (Exo/exo isomer to endo-lendo isomer ratio was 97:3 by $^1$H-NMR analysis.)

Example 2

Synthesis of NB-di-F—OH

A 2 L flask was charged with 18 g (0.75 mol) of sodium hydride and 800 mL of anhydrous THF inside a dry box. A solution of 42 g (0.33 mol) of 2,3-dihydroxynorborn-5-ene (prepared as described in Example 1 and dried under dynamic vacuum at 40-50° C. for 3 hr) in 400 mL of dry THF was slowly added to the agitated suspension of NaH (95%, Sigma-Aldrich Chemical Company) in THF over ~2 h to maintain the internal temperature of the reaction mixture at 25-30° C. After the addition was finished, the reaction mixture was agitated at 30-40° C. for an additional hour, and then a solution of 125 g (0.69 mol) of HFIBO was added slowly dropwise at 30-35° C. over 30 min. The reaction mixture was slowly brought to 60° C. A slightly exothermic reaction was observed, and the internal temperature of the reaction mixture was slowly increased to 68° C. (~2 hr). The reaction mixture was kept at reflux until all of the starting diol was consumed (as determined by GC), ~4-5 hr. After agitating overnight, 20 ml of methanol was added to the reaction mixture and the solvent was removed under vacuum. 300 mL of dichloromethane was added to the crude solid product (~230 g). The suspension was cooled to 0° C. and ~300 mL of a mixture of 50 mL conc. HCl in 250 mL of water was added dropwise to bring the pH of the reaction mixture to ~1-2. The organic layer was separated, washed with water (2×500 mL), and dried over MgSO$_4$. The solvent was removed under vacuum and the residue was distilled under vacuum using a short path distillation head. The product crystallized on standing. There was isolated 140.7 g (87%) of crystalline material (b.p. 92-99° C., main fraction-97-99° C.; m.p. 51-52° C.), identified by NMR as NB-di-F—OH (>98% purity, mixture of exo-exo- and endo-endo-isomers in the ratio 96:4). $^1$H NMR (CDCl$_3$, major isomer): 1.6 (1H, d, J=10 Hz), 1.8 (1H, d, J=10 Hz), 2.7 (2H, pent. J=1.9 Hz), 3.4 (2H, s), 3.8 (2H, dq, J=10.5, 1.6 Hz), 3.9 (2H, d, J=10.5 Hz), 4.7 (2H, br. s), 6.0 (2H, t, J=1.9 Hz) ppm; $^{19}$F (CDCl$_3$, major isomer): −76.6(3F, q, J=9.1 Hz), −77.30(3F, g, J=9.1 Hz) ppm; $^{13}$C ({H}, neat major isomer): 43.6, 45.5, 66.0, 75.1 (hept, J=29.1 Hz), 77.8, 122.2(q, J=284 Hz), 122.3(q, J=284 Hz), 136.7 ppm.

Example 3

Synthesis of TCN-di-F—OH

A. Synthesis of Tricyclo[4.2.1.0$^{2,5}$]non-7-ene-trans-3,4-dicarboxylic acid dimethyl ester To a 500 mL round-bottom flask equipped with a stir bar, thermometer, reflux condenser, and nitrogen inlet were added dimethyl fumarate (62.0 g, 0.430 mol) and quadricyclane (47.6 g, 0.512 mol). The mixture was heated at 110° C. for 20 hr. Dimethyl fumarate completely dissolved in quadricyclane when the temperature reached 80° C., resulting in a clear yellow solution. GC analysis of the reaction mixture showed no trace of dimethyl fumarate, and excess quadricyclane was evaporated under vacuum and collected in a cold trap (liquid nitrogen). This yielded a white solid (100 g, 98%). The crude material (>98% purity by GC) was used in the next step without further purification. $^1$H-NMR (ppm, CDCl$_3$): δ 1.27 (1H, dt, J=10.0, 1.5 Hz), 1.46 (1H, d, J=10.0 Hz), 2.10 (1H, t, J=5.0 Hz), 2.27 (1H, t, J=8.0 Hz), 2.83 (1H, s), 2.87 (1H, dd, J=7.5, 5.0 Hz), 2.88 (1H, s), 3.60 (1H, dd, J=9.5, 7.5 Hz), 3.69 (6H, s), 5.98 (2H, m).

B. Synthesis of Tricyclo[4.2.1.0$^{2,5}$]non-7-ene-trans-3,4-dimethanol

To a 100 mL three-neck round-bottom flask equipped with a stir bar, thermometer, addition funnel, and nitrogen inlet were added tricyclo[4.2.1.0$^{2,5}$]non-7-ene-trans-3,4-dicarboxylic acid dimethyl ester (5.0 g, 21.2 mmol) and THF (20 mL). The solution was cooled to 0° C. with an ice/water bath, and lithium aluminum hydride (12.7 mL of 1 M solution in THF, 1.2 equiv) was added dropwise. The reaction mixture was warmed to room temperature and stirred for 18 h. The reaction was carefully quenched by adding the reaction mixture to a solution of saturated ammonium chloride in water (50 mL). The pH of the aqueous portion was adjusted to 7. The product was extracted with ethyl acetate (3×20 mL). The combined organics were washed once with water and brine, dried with magnesium sulfate, filtered, and evaporated to yield a yellow oil (3.66 g, 96%). The crude oil (>98% purity by GC) was used in the next step without further purification. $^1$H-NMR (ppm, CDCl$_3$): δ 1.27(1H, dp, J=9.2, 1.6 Hz), 1.63 (1H, m), 1.73 (1H, m), 1.83 (1H, p, J=2.0 Hz), 1.94 (1H, t, J=8.4 Hz), 2.28 (1H, m), 2.52 (2H, bs, OH), 2.69 (2H, s), 3.43 (1H, t, J=10.0 Hz), 3.65 (4H, m), 5.94 (2H, m). $^{13}$C-NMR (ppm, CDCl$_3$): δ 36.1, 36.9, 40.0, 41.3, 41.4, 42.9, 44.0, 60.9, 67.1, 135.3, 136.8.

C. Synthesis of TCN-di-FOH

To a 250 mL three-neck round-bottom flask equipped with a stir bar, thermometer, addition funnel, reflux condenser, and nitrogen inlet were added sodium hydride (1.46 g, 61.0 mmol) and anhydrous THF (30 mL). The mixture was cooled to 0° C. with an ice/water bath, and a solution of tricyclo [4.2.1.0$^{2,5}$]non-7-ene-trans-3,4-dimethanol (5.0 g, 27.7 mmol) and THF (50 mL) was added dropwise. The reaction mixture was maintained at 0° C. and HFIBO (11.0 g, 61.0 mmol) in THF (50 mL) was added dropwise. The reaction mixture was stirred at room temperature for 1 hr and then heated to 65° C. for 5 hr. After heating, the mixture became a homogeneous solution. GC analysis showed complete disappearance of the starting diol and appearance of two peaks for the two product diastereomers. The reaction was carefully quenched by adding 1 M hydrochloric acid until the pH of the aqueous portion was 6. The product was extracted with ethyl acetate (3×50 mL). The combined organics were washed once with water and brine, dried with magnesium sulfate, filtered, and evaporated. The crude oil was vacuum distilled (121-122° C./0.10 torr) to obtain a colorless oil (9.78 g, 65%). $^1$H-NMR (ppm, CDCl$_3$): δ1.33 (1H, d, J=8.5 Hz), 1.55 (1H, d, J=10.0 Hz), 1.57 (1H, s), 1.69 (1H, t, J=5.5 Hz), 1.82 (1H, p, J=5.5 Hz), 1.97 (1H, t, J=8.5 Hz), 2.41 (1H, p, J=9.0 Hz), 2.71 (2H, s), 3.52 (1H, t, J=8.5 Hz), 3.58 (1H, t, J=8.5 Hz), 3.69 (2H, m), 3.81 (3H, m), 4.41 (1H, s), 4.45 (1H, s), 5.97 (2H, m). $^{19}$F-NMR (ppm, CDCl$_3$): δ −76.99 (3F, p, J=8.7 Hz), −77.06

(3F, p, J=7.9 Hz), −77.07 (6F, s). $^{13}$C-NMR (ppm, CDCl$_3$): δ 35.7, 36.1, 37.7, 38.0, 41.2, 42.6, 43.8, 66.6, 71.9, 77.2, 135.5, 136.6.

Example 4

Synthesis of a TFE and TCN-di-F—OH Copolymer

A 400 mL pressure vessel was swept with nitrogen and charged with 67.5 g (0.125 mol) of TCN-di-F—OH, 50 mL of Solkane® 365 mfc and 1.20 g of Perkadox®16N. The vessel was closed, cooled in dry ice, evacuated, and charged with 30 g (0.30 mol) of TFE. The vessel contents were heated to 50° C. and agitated for 18 hr as the internal pressure decreased from 268 psi to 237 psi. The vessel was cooled to room temperature and vented to one atmosphere. The vessel contents were added to excess hexane. The solid was filtered, washed with hexane, dissolved in THF and precipitated in hexane. This solid was filtered and dried in a vacuum oven at about 80° C. There was isolated 33.3 g of the white copolymer. Its fluorine NMR spectrum showed peaks at −72 to −76 from CF$_3$ groups of the TCN-di-F—OH and absorption at −95 to −125 from CF$_2$ groups of the TFE component. GPC analysis: Mn=11000, Mw=20000, Mw/Mn=1.82. DSC: Tg at 87° C. Anal. Found: C, 39.57; H, 3.07; F, 44.74.

Example 5

Synthesis of a TFE and NB-di-F—OH Copolymer

A 400 mL pressure vessel was swept with nitrogen and charged with 97.2 g (0.20 mol) of NB-di-F—OH, 50 mL of Solkane® 365 mfc and 1.90 g of Perkadox®16N. The vessel was closed, cooled in dry ice, evacuated, and charged with 40 g (0.40 mol) of TFE. The vessel contents were heated to 50° C. and agitated for 18 hr as the internal pressure decreased from 326 psi to 316 psi. The vessel was cooled to room temperature and vented to one atmosphere. The vessel contents were added to excess hexane. The solid was filtered, washed with hexane, dissolved in THF and precipitated in hexane. This solid was filtered and dried in a vacuum oven at about 80° C. There was isolated 11.0 g of the white copolymer. Its fluorine NMR spectrum showed peaks at −72 to −76 from CF$_3$ groups of the NB-di-F—OH and absorption at −95 to −125 from CF$_2$ groups of the TFE component. GPC analysis: Mn=4100, Mw=5500, Mw/Mn=1.82. DSC: Tg at 138° C. Anal. Found: C, 36.25; H, 2.72; F, 46.31.

Example 6

Synthesis of a TFE and NB-di-F—OH Copolymer

A metal pressure vessel of approximate 270 mL capacity was charged with 111.67 g NB-di-F—OH and 75 mL Solkane® 365 mfc. The vessel was closed, cooled to about −15° C. and pressured to 400 psi with nitrogen and vented several times. The reactor contents were heated to 50° C. TFE was added to a pressure of 340 psi and a pressure regulator was set to maintain the pressure at 340 psi throughout the polymerization by adding TFE as required. A 0.21 molar solution of HFPO-dp in Solkane® 365 mfc was pumped into the reactor at a rate of 1.5 mL/minute for 6 minutes, and then at a rate of 0.07 mL/minute for 8 hours. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was twice dissolved in a mixture of THF and Solkane® 365 mfc and added slowly to excess hexane. The precipitate was filtered, washed with hexane and dried in a vacuum oven overnight to give 66.0 g of white polymer. GPC: Mn=9000; Mw=19600; Mw/Mn=2.18. Anal. Found: C, 34.71; H, 1.96; F, 52.49. Fluorine NMR shows that the polymer contains 54% TFE units and 46% NB-di-F—OH units.

Example 7

Synthesis of a TFE, NB—F—OH and NB-di-F—OH Terpolymer

A metal pressure vessel of approximate 270 mL capacity was charged with 50.8 g (0.175 mol) of NB—F—OH, 36.5 g (0.075 mol) of NB-di-F—OH and 75 mL Solkane® 365 mfc. The vessel was closed, cooled to about −15° C., and pressured to 400 psi with nitrogen and vented several times. The reactor contents were heated to 50° C. TFE was added to a pressure of 340 psi and a pressure regulator was set to maintain the pressure at 340 psi throughout the polymerization by adding TFE as required. A 0.21 molar solution of HFPO-dp in Solkane® 365 mfc was pumped into the reactor at a rate of 1.5 mL/minute for 6 minutes, and then at a rate of 0.07 mL/minute for 8 hours. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was dissolved in a mixture of THF and Solkane® 365 mfc and added slowly to excess hexane. The precipitate was filtered, washed with hexane and dried in a vacuum oven overnight to give 52.6 g of white polymer. GPC: Mn=12400; Mw=19400; Mw/Mn=1.58. DSC: Tg at 145° C. A $^{13}$C NMR analysis showed the composition to be 55% TFE, 34% NB—F—OH and 11% NB-di-F—OH. Anal. Found: C, 37.89; H, 2.58; F, 44.38.

Example 8

Synthesis of a TFE, NB—F—OH and NB-di-F—OH Terpolymer

A metal pressure vessel of approximate 270 mL capacity was charged with 29.0 g (0.10 mol) of NB—F—OH, 59.25 g (0.12 mol) of NB-di-F—OH and 75 mL Solkane® 365 mfc. The vessel was closed, cooled to about −15° C., and pressured to 400 psi with nitrogen and vented several times. The reactor contents were heated to 50° C. TFE was added to a pressure of 340 psi and a pressure regulator was set to maintain the pressure at 340 psi throughout the polymerization by adding TFE as required. A 0.21 molar solution of HFPO-dp in Solkane® 365 mfc was pumped into the reactor at a rate of 1.5 mL/minute for 6 minutes, and then at a rate of 0.07 mL/minute for 8 hours. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was dissolved in a mixture of THF and Solkane® 365 mfc and added slowly to excess hexane. The precipitate was filtered, washed with hexane and dried in a vacuum oven overnight to give 50.6 g of white polymer. GPC: Mn=12600; Mw=19900; Mw/Mn=1.58. DSC: Tg at 149° C. A $^{13}$C NMR analysis showed the composition to be 55% TFE, 26% NB—F—OH and 18% NB-di-F—OH. Anal. Found: C, 36.41; H, 2.30; F, 47.25.

Example 9

Synthesis of a TFE. NB—F—OH and NB-di-F—OH Terpolymer

A metal pressure vessel of approximate 270 mL capacity was charged with 18.13 g (0.0625 mol) of NB—F—OH, 91.13 g (0.1875 mol) of NB-di-F—OH and 75 mL Solkane® 365 mfc. The vessel was closed, cooled to about −15° C., and pressured to 400 psi with nitrogen and vented several times. The reactor contents were heated to 50° C. TFE was added to a pressure of 340 psi and a pressure regulator was set to maintain the pressure at 340 psi throughout the polymerization by adding TFE as required. A 0.21 molar solution of HFPO-dp in Solkane® 365 mfc was pumped into the reactor at a rate of 1.5 mL/minute for 6 minutes, and then at a rate of 0.07 mL/minute for 8 hours. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was dissolved in a mixture of THF and Solkane® 365 mfc and added slowly to excess hexane. The precipitate was filtered, washed with hexane and dried in a vacuum oven overnight to give 77.4 g of white polymer. GPC: Mn=6800; Mw=18000; Mw/Mn=1.58. DSC: Tg at 137° C. Anal. Found: C, 35.72; H, 2.22; F, 48.88.

Example 10

Synthesis of a Methoxymethyl Ether Protected TFE/TCN-di-F—OH Copolymer

A 8.0 g sample of the TFE/TCN-di-F—OH copolymer, prepared in Example 4, was charged under nitrogen to a 100 mL round bottom flask equipped with a dry ice condenser. To the flask was added 50 mL acetonitrile and 10.35 g anhydrous sodium carbonate. The mixture was heated to 80° C. for 20 minutes. It was cooled to 40° C. and 1.006 g of chloromethyl methyl ether (Sigma-Aldrich Chemical Company) was added dropwise. The resulting mixture was maintained at 40-50° C. for 3 hr and stirred overnight at room temperature. The reaction mixture was poured into 700 mL of 1% hydrogen chloride in water. The precipitate that formed was collected and washed with water. It was dissolved in 50 mL acetone and added to 700 mL of 1% hydrogen chloride in water. The precipitate was collected and dried overnight in a vacuum oven at 100° C., giving 7.3 g of polymer. Fluorine NMR spectrum indicted that about 44% of the fluoroalcohol groups were converted to methoxy methyl ethers.

Example 11

Synthesis of a Methoxymethyl Ether Protected TFE/TCN-di-F—OH Copolymer

The procedure of Example 10 was followed except that the amount of chloromethyl methyl ether was decreased to 0.553 g. There was isolated 7.6 g of polymer. Its fluorine NMR spectrum indicated that about 25% of the fluoroalcohol groups were converted to methoxy methyl ethers.

Example 12

Synthesis of a Methoxymethyl Ether Protected TFE/NB-di-F—OH Copolymer

To a 250 mL three-neck round-bottom flask equipped with a magnetic stir bar, thermometer, $N_2$ inlet, addition funnel, and dry ice condenser were added TFE/NB-di-FOH polymer of Example 6 (10.0 g, 34.1 mmol, based on equivalent weight of 293 g/mol per OH), $K_2CO_3$ (14.1 g, 102 mmol), and acetonitrile (68 mL). This peach-colored mixture was heated to 80° C. for 20 min using an oil bath equipped with a thermocouple, and remained a heterogeneous mixture. The mixture was then cooled to 45° C., at which time chloromethyl methyl ether (0.82 g, 10.2 mmol) was added dropwise. The milky white heterogeneous mixture was heated at 45° C. for 3 h, then stirred at room temperature overnight. The mixture was then precipitated into 700 mL of a 1% HCl solution. The pH of the solution was determined to be slightly acidic (5-6). The precipitate was then vacuum filtered, washed with water, and air-dried. The dried polymer was redissolved into 50 mL acetone. This homogenous solution was then acidified with 0.5 mL of 37% HCl solution. The solution was then vacuum filtered to remove any precipitated salts. The filtrate was then re-precipitated into 700 mL of 1% HCl solution, vacuum filtered, and washed with water until the pH of the water filtrate was neutral. The polymer was air dried and then thoroughly dried in a vacuum oven at 100° C. for at least 3-4 h. This procedure afforded a white, fluffy polymer (9.2 g, 40%). The percent of MOM protection was determined via $^{19}$F-NMR analysis: 23%. The molecular weight and polydispersity were determined by SEC analysis relative to polystyrene standards: $M_w$=19,400; PDI=1.97. DSC analysis showed a $T_g$ of 129° C. Thermal decomposition temperature at 10 wt % lost was determined to be 362° C. by TGA.

Example 13

Synthesis of a Methoxymethyl Ether Protected TFE/NB-di-F—OH Copolymer

The procedure of Example 12 was followed using 0.6 equivalents of chloromethyl methyl ether (1.7 g, 0.020 mmol). The percent of MOM protection was determined via $^{19}$F-NMR analysis: 39%. The molecular weight and polydispersity were determined by SEC analysis relative to polystyrene standards: $M_w$=19,300; PDI=1.95. DSC analysis showed a $T_g$ of 126° C. Thermal decomposition temperature at 10 wt % lost was determined to be 375° C. by TGA.

Example 14

Synthesis of a Methoxymethyl Ether Protected TFE/NB—F—OH/NB-di-F—OH Terpolymer A 10 g sample of the TFE/NB—F—OH/NB-di-F—OH terpolymer prepared in Example 8 was charged under nitrogen to a 100 mL round bottom flask equipped with a dry ice condenser. To the flask was added 50 mL acetonitrile and 13.8 g anhydrous sodium carbonate. The mixture was heated to reflux for 30 minutes. It was cooled to 40° C. and 1.00 g of chloromethyl methyl ether (Sigma-Aldrich Chemical Company) was added dropwise. The resulting mixture was maintained at 50° C. for 3 hr and stirred overnight at room temperature. The reaction mixture was poured into 700 mL of 1% hydrogen chloride in water. The precipitate that formed was collected and washed with water. It was dissolved in 30 mL acetone and added to 700 mL of 1% hydrogen chloride in water. The precipitate was collected and dried overnight in a vacuum oven at 100° C. giving 9.27 g of polymer. Fluorine NMR spectrum indicted that about 32% of the fluoroalcohol groups were converted to methoxy methyl ethers. GPC: $M_n$=13900; $M_w$=21900; $M_w/M_n$=1.58. DSC: $T_g$=135° C.

Example 15

Synthesis of a Methoxymethyl Ether Protected TFE/NB—F—OH/NB-di-F—OH Terpolymer

The procedure of Example 14 was followed except that the amount of chloromethyl methyl ether was decreased to 0.50 g. There was isolated 9.57 g of polymer. Its fluorine NMR spectrum indicated that about 19% of the fluoroalcohol groups were converted to methoxy methyl ethers. GPC: $M_n$=14400; $M_w$=21700; $M_w/M_n$=1.51. DSC: $T_g$=141° C.

Example 16

Synthesis of a Methoxymethyl Ether Protected TFE/NB—F—OH/NB-di-F—OH Terpolymer

A 20 g sample of the TFE/NB—F—OH/NB-di-F—OH terpolymer prepared in Example 9 was charged under nitrogen to a 300 mL round bottom flask equipped with a dry ice condenser and addition funnel. To the flask was added 1 L acetonitrile and 27.0 g anhydrous potassium carbonate. The mixture was heated to reflux for 30 minutes. It was cooled to 40° C. and 2.10 g of chloromethyl methyl ether (Sigma-Aldrich Chemical Company) was added dropwise. The resulting mixture was maintained at 50° C. for 3 hr and stirred overnight at room temperature. The reaction mixture was poured into 700 mL of 1% hydrogen chloride in water. The precipitate that formed was collected and washed with water. It was dissolved in 100 mL acetone and added to 1600 mL of 1% hydrogen chloride in water. The precipitate was collected and dried overnight in a vacuum oven at 90° C., giving 18.5 g of polymer. Fluorine NMR spectrum indicted that about 38% of the fluoroalcohol groups were converted to methoxy methyl ethers.

Example 17

Synthesis of a Methoxymethyl Ether Protected TFE/NB—F—OH/NB-di-F—OH Terpolymer

The procedure of Example 16 was followed except that the amount of chloromethyl methyl ether was decreased to 1.05 g. There was isolated 19.2 g of polymer. Its fluorine NMR spectrum indicated that about 17% of the fluoroalcohol groups were converted to methoxy methyl ethers.

Example 18

Synthesis of an Adamantylmethoxymethyl Ether Protected TFE/NB-di-F—OH Copolymer

The procedure of Example 16 was followed except that a 20 g sample of TFE/NB-di-F—OH copolymer, prepared as in Example 6, was used, and the chloromethyl methyl ether was replaced with 2.92 g of 1-(chloromethoxymethyl)adamantane (Idemitsu Chemical USA, Southfield, Mich.). There was isolated 17.6 g of polymer. Its fluorine NMR spectrum indicated that about 16% of the fluoroalcohol groups were converted to adamantylmethoxy methyl ether groups.

Example 19

Synthesis of an Adamantylmethyoxymethyl Ether Protected TFE/NB-di-F—OH Copolymer The procedure of Example 18 was followed except that the amount of 1-(chloromethoxymethyl)adamantane was increased to 7.29 g. There was isolated 24.1 g of polymer. Its fluorine NMR spectrum indicated that about 46% of the fluoroalcohol groups were converted to adamantylmethoxy methyl ether groups.

Example 20

Synthesis of a TFE/NB-di-F—OH/MAdA Ternolymer

A metal pressure vessel of approximate 270 mL capacity was charged with 89.42 g NB-di-F—OH, 3.52 g MAdA and 25 mL Solkane® 365 mfc. The vessel was closed, cooled to about −15° C., and pressured to 400 psi with nitrogen and vented several times. The reactor contents were heated to 50° C. TFE was added to a pressure of 280 psi and a pressure regulator was set to maintain the pressure at 280 psi throughout the polymerization by adding TFE as required. A solution of 4.87 g Perkadox®16N dissolved in 40 mL methyl acetate and diluted to 100 mL with Solkane® 365 mfc was pumped into the reactor at a rate of 2.0 mL/minute for 6 minutes, and then at a rate of 0.1 mL/minute for 8 hours. At the same time, a solution prepared by diluting 70.20 g B-di-F—OH and 29.33 g MAdA to 100 mL with Solkane® 365 mfc was pumped into the reactor at 0.10 mL/min for 12 hr. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was twice dissolved in a mixture of THF and Solkane® 365 mfc and added slowly to excess hexane. The precipitate was filtered, washed with hexane and dried in a vacuum oven overnight to give 47.9 g of white polymer. GPC: $M_n$=7500; $M_w$=12000; $M_w/M_n$=1.59. A $^{13}$C NMR analysis showed the composition to be 23% TFE, 33% NB-di-F—OH and 45% MAdA. Anal. Found: C, 48.57; H, 4.69; F, 31.87.

Example 21

Synthesis of a TFE/NB-di-F—OH/PinAc/HAdA Tetrapolymer

A metal pressure vessel of approximate 270 mL capacity was charged with 89.42 g NB-di-F—OH, 1.38 g PinAc, 1.78 g HAdA and 25 mL methyl acetate. The vessel was closed, cooled to about −15° C., and pressured to 400 psi with nitrogen and vented several times. The reactor contents were heated to 50° C. TFE was added to a pressure of 280 psi and a pressure regulator was set to maintain the pressure at 280 psi throughout the polymerization by adding TFE as required. A solution of 1.77 g Perkadox®16N dissolved in 40 mL methyl acetate and diluted to 100 mL with Solkane® 365 mfc was pumped into the reactor at a rate of 2.0 mL/minute for 6 minutes, and then at a rate of 0.1 mL/minute for 8 hours. At the same time, a solution prepared by diluting 70.20 g NB-di-F—OH, 11.47 g PinAc and 14.80 g HAdA to 100 mL with methyl acetate was pumped into the reactor at 0.10 mL/min for 12 hr. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was twice dissolved in a mixture of THF and Solkane® 365 mfc, and added slowly to excess hexane. The precipitate was filtered, washed with hexane and dried in a vacuum oven overnight to give 47.9 g of white polymer. GPC: $M_n$=9300; $M_w$=18400; $M_w/M_n$=1.98. Anal. Found: C, 46.72; H, 4.66; F, 30.69.

Example 22

Synthesis of a NB-di-F—OH/PinAc/HAdA Terpolymer

A round bottom flask was purged with nitrogen and charged with 43.74 g NB-di-F—OH, 0.86 g PinAc, 1.11 g HAdA and 20 mL ethyl acetate. This solution was heated to 80° C. and a solution of 24.30 g NB-di-F—OH, 4.3 g PinAc, 5.55 g HAdA, 0.77 g Vazo®67 and 40 mL ethyl acetate was added dropwise over 2.5 hr. After addition was complete, the solution was maintained at 80° C. for 3 hr and then allowed to cool to room temperature overnight. The reactor mixture was diluted with 50 mL ethyl acetate and poured with stirring into 1600 mL hexane. The solid polymer was filtered, dissolved in 100 mL THF and precipitated into 1600 mL hexane. The polymer was filtered, washed with hexane and dried overnight in a vacuum oven. There was isolated 19.5 g of polymer. GPC: $M_n$=5300, $M_w$=9200, $M_w/M_n$=1.73. A $^{13}$C NMR analysis showed the composition to be 28% NB-di-F—OH, 34% PinAc and 39% HAdA.

Example 23

Synthesis of a NB-di-F—OH/PinAc/MAdA/HAdA Terpolymer

A round bottom flask was purged with nitrogen and charged with 43.74 g NB-di-F—OH, 0.522 g PinAc, 0.22 g MAdA, 1.33 g HAdA and 20 mL ethyl acetate. This solution was heated to 80° C. and a solution of 24.30 g NB-di-F—OH, 2.58 g PinAc, 1.10 g MAdA, 6.66 g HAdA, 0.77 g Vazo®67 and 40 mL ethyl acetate was added dropwise over 2.5 hr. After addition was complete, the solution was maintained at 80° C. for 3 hr and then allowed to cool to room temperature overnight. The reactor mixture was diluted with 50 mL ethyl acetate and poured with stirring into 1600 mL hexane. The solid polymer was filtered, dissolved in 100 mL THF and precipitated into 1600 mL hexane. The polymer was filtered, washed with hexane and dried overnight in a vacuum oven. There was isolated 19.7 g of polymer. GPC: $M_n$=4600, $M_w$=7400, $M_w/M_n$=1.62. A $^{13}$C NMR analysis showed the composition to be 26% NB-di-F—OH, 19% PinAc, 11% MAdA and 44% HAdA.

Example 24

Synthesis of a NB-di-F—OH/MAdA/GBLA/HAdA Terpolymer

A round bottom flask was purged with nitrogen and charged with 38.88 g NB-di-F—OH, 1.76 g MAdA, 1.25 g GBLA, 0.89 g HAdA and 20 mL ethyl acetate. This solution was heated to 80° C. and a solution of 19.44 g NB-di-F—OH, 5.28 g MAdA, 3.74 g GBLA, 2.66 g HAdA, 0.77 g Vazo®67 and 40 mL ethyl acetate was added dropwise over 2.5 hr. After addition was complete, the solution was maintained at 80° C. for 3 hr and then allowed to cool to room temperature overnight. The reactor mixture was diluted with 50 mL ethyl acetate and poured with stirring into 1600 mL hexane. The solid polymer was filtered, dissolved in 100 mL THF, and precipitated into 1600 mL hexane. The polymer was filtered, washed with hexane and dried overnight in a vacuum oven. There was isolated 22.4 g of polymer. GPC: $M_n$=6600, $M_w$=13400, $M_w/M_n$=2.03. A $^{13}$C NMR analysis showed the composition to be 21% NB-di-F—OH, 31% MAdA, 32% GBLA and 16% HAdA.

Example 25

Photoresist Prepared from a Methoxymethyl Ether Protected TFE/TCN-di-F—OH Copolymer The following formulation was prepared and magnetically stirred overnight:

| Component | Wt. (gm) |
|---|---|
| TFE/TCN-di-F-OH/TCN-di-F-OMOM polymer of Example 10 | 0.570 |
| 2-Heptanone | 3.990 |
| 6.82 wt % solution of triphenylsulfonium nonaflate dissolved in 2-heptanone that had been filtered through a 0.45 µm PTFE syringe filter. | 0.440 |

The wafer was prepared by applying a hexamethyldisilazane (HMDS) primer layer using a YES-3 vapor prime oven. A 100% HMDS adhesion promoter from Arch Chemical Co. was used. The oven was set to give a prime at 150° C. for 300 sec.

The sample was spin coated using a Brewer Science Inc. Model-100CB combination spin coater/hotplate on a 4 in. diameter Type "P", <100> orientation, silicon wafer. To prepare the coating, 2 ml of the above solution, after filtering through a 0.45 µm PTFE syringe filter, was deposited and spun at 2500 rpm for 60 sec, and then baked at 150° C. for 60 sec.

248 nm imaging was accomplished by exposing the coated wafer to light obtained by passing broadband UV light from an ORIEL Model-82421 Solar Simulator (1000 watt) through a 248 nm interference filter which passes about 30% of the energy at 248 nm. Exposure time was 2 sec, providing an unattenuated dose of 3 mJ/cm$^2$. By using a mask with 18 positions of varying neutral optical density, a wide variety of exposure doses were generated. After exposure the exposed wafer was baked at 105° C. for 60 sec.

The wafer was tray developed for 60 sec in aqueous 2.38 wt % tetramethylammonium hydroxide (TMAH) solution (Shipley LDD-026W, Marlborough, Mass.).

This test generated a positive image with a clearing dose of ~0.7 mJ/cm$^2$.

Example 26

Photoresist Prepared from a Methoxymethyl Ether Protected TFE/TCN-di-F—OH Copolymer A formulation was prepared as in Example 25, except that the TFE/TCN-di-F—OH/TCN-di-F-OMOM polymer used was that prepared in Example 11.

It was processed as in Example 25, except that the spin speed for the formulation was 1500 rpm. This test generated a partially cleared positive image with a dose of ~0.7 mJ/cm$^2$.

Example 27

Photoresist Prepared from a Methoxymethyl Ether Protected TFE/NB-di-F—OH Copolymer The following formulation was prepared and magnetically stirred overnight:

| Component | Wt. (gm) |
|---|---|
| TFE/NB-di-F-OH/NB-di-F-OMOM polymer of Example 12 | 2.202 |
| 2-Heptanone | 14.741 |
| Solution of tetrabutylammonium lactate in 2-heptanone prepared as follows: 2.5 gm of aqueous tetrabutylammonium hydroxide (40%, Sigma-Aldrich Chemical Company) was dissolved in 97.5 gm ethyl lactate (Sigma-Aldrich Chemical Company). 6.0 gm of this solution was later dissolved in 6.0 gm of 2-heptanone. | 0.92 |
| 6.82 wt % solution of triphenylsulfonium nonaflate dissolved in 2-heptanone that had been filtered through a 0.45 µm PTFE syringe filter. | 1.137 |

The formulation was processed as in Example 25, except that the priming oven was programmed to give a prime at 150-300° C. for 160 sec, and an overall exposure of 15 sec was used to give a dose of 22.5 mJ/cm². This test generated a positive image with a clearing dose of ~2.2 mJ/cm².

Example 28

Photoresist Prepared from a Methoxymethyl Ether Protected TFE/NB—F—OH/NB-di-F—OH Terpolymer A formulation was prepared as in Example 27, except that the TFE/NB-di-F—OH/NB-di-F-OMOM polymer used was prepared in Example 13.

The formulation was processed as in Example 27. This test generated a positive image with a clearing dose of ~2.2 mJ/cm².

Example 29

Photoresist Prepared from a Methoxymethyl Ether Protected TFE/NB—F—OH/NB-di-F—OH Terpolymer A formulation was prepared as in Example 27, except that the polymer was a partially protected TFE/NB—F—OH/NB-di-F—OH polymer as prepared in Example 14.

The formulation was processed as in Example 27. This test generated a positive image with a clearing dose of ~3.6 mJ/cm².

Example 30

Photoresist Prepared from a Methoxymethyl Ether Protected TFE/NB—F—OH/NB-di-F—OH Ternolymer A formulation was prepared as in Example 29, except that the polymer was a partially protected TFE/NB—F—OH/NB-di-F—OH polymer as prepared in Example 15.

The formulation was processed as in Example 29. This test generated a positive image with a clearing dose of ~2.2 mJ/cm².

Example 31

Photoresist Prepared from a Methoxymethyl Ether Protected TFE/NB—F—OH/NB-di-F—OH Terpolymer The following formulation was prepared and magnetically stirred overnight:

| Component | Wt. (gm) |
|---|---|
| TFE/NB-F-OH/NB-di-F-OH partially protected polymer of Example 16 | 1.101 |
| 2-Heptanone | 7.370 |
| Solution of tetrabutylammonium lactate in 2-heptanone prepared as follows: 2.5 gm of aqueous tetrabutylammonium hydroxide (40%, Sigma-Aldrich Chemical Company) was dissolved in 97.5 gm ethyl lactate (Sigma-Aldrich Chemical Company). 2.50 gm of this solution was later dissolved in 2.50 gm of 2-heptanone. | 0.460 |
| 6.82 wt % solution of triphenylsulfonium nonaflate dissolved in 2-heptanone that had been filtered through a 0.45 µm PTFE syringe filter. | 0.568 |

The formulation was processed as in Example 27, except with a post exposure bake of 105° C. This test generated a positive image with a clearing dose of ~2.2 mJ/cm².

Example 32

Photoresist Prepared from a Methoxymethyl Ether Protected TFE/NB—F—OH/NB-di-F—OH Terpolymer A formulation was prepared as in Example 31, except that the partially protected TFE/NB—F—OH/NB-di-F—OH polymer was prepared in Example 17.

The formulation was processed as in Example 31. This test generated a positive image with a clearing dose of ~2.2 mJ/cm².

Example 33

Photoresist Prepared from an Adamantylmethoxymethyl Ether Protected TFE/NB-di-F—OH Copolymer The following formulation was prepared and magnetically stirred overnight:

| Component | Wt. (gm) |
|---|---|
| TFE/NB-di-F-OH/NB-di-F-OMOAd polymer of Example 18 | 0.927 |
| 2-Heptanone | 6.594 |
| 6.82 wt % solution of triphenylsulfonium nonaflate dissolved in 2-heptanone that had been filtered through a 0.45 µm PTFE syringe filter. | 0.479 |

The formulation was processed as in Example 27, except for the following conditions: a post exposure bake of 135° C. for 60 sec; an exposure time of 60 sec for a dose of 90 mJ/cm²; and a development time of 10 sec.

The sample showed significant dark development (unexposed thickness changed from 1511 nm to 250 on development).

Example 34

Photoresist Prepared from an Adamantylmethyoxymethyl Ether Protected TFE/NB-di-F—OH Copolymer A formulation was prepared as in Example 33, except that the partially protected TFE/NB-di-F—OH/NB-di-F-OMOAd polymer was prepared in Example 19.

The formulation was processed as in Example 27, except that an exposure time of 2 sec was used to give an overall dose of 3 mJ/cm$^2$. This test generated a positive image with a clearing dose of ~0.29 mJ/cm$^2$.

Example 35

Photoresist Prepared from a TFE/NB-di-F—OH/MAdA Terpolymer

A formulation was prepared as in Example 31, except that the polymer was the TFE/NB-di-F—OH/MAdA polymer prepared in Example 20.

The formulation was processed as in Example 31, except with a post exposure bake of 135° C., and a development time of 20 sec.

It generated a positive image with a clearing dose of 2.2 mJ/cm$^2$.

Example 36

Photoresist Prepared from a TFE/NB-di-F—OH/PinAc/HAdA Tetrapolymer

A formulation was prepared as in Example 35, except that the polymer was the TFE/NB-di-F—OH/PinAc/HAdA polymer prepared in Example 21. The formulation was processed as in Example 35. The sample showed substantial dark development.

Example 37

Absorption Measurements at 157 nm

Absorption measurements were made by the procedure described in the "Examples" section, above.

The polymers of this invention showed low absorption at 157 nm as indicated in the data summarized below.

| POLYMER (Ex #) | ABSORPTION (at 157 nm, μm$^{-1}$) |
|---|---|
| 4 | 1.24 |
| 5 | 0.75 |
| 6 | 0.47 |
| 8 | 0.55 |
| 10 | 1.47 |
| 11 | 1.47 |
| 12 | 0.63 |
| 13 | 0.66 |
| 14 | 0.65 |
| 15 | 0.66 |

Example 38

Effect of NB-di-F—OH on Dissolution Rates

Measurements were made to determine the effect on dissolution rates of incorporating the NB-di-F—OH monomer into polymers.

Dissolution rate measurements were made on thin films of the polymer solution that had been spin-coated on Si wafers. Spin coating was done using a Brewer Science Inc. Model-100CB combination spin coater/hotplate. 4 in. diameter Type "P", <100> orientation, silicon wafers were prepared for coating by vapor depositing HMDS primer using a Yield Engineering Systems vapor prime oven for 5 min at 150° C.

Dissolution rates were measured using a Luzchem TFA-11 thin film analyzer. This analyzer uses a multi-wavelength diode array detector to monitor sample reflectivity as a function of time when developer is applied to the sample. In these tests, a standard lithographic developer (Shipley LDD26W-0.26N) was used. In instances where development was too fast to be tracked by the analyzer, the developer was diluted to slow development. In these cases, several different dilutions were used to allow an extrapolation to effect of using full strength developer.

To highlight the effect of incorporating the NB-di-F—OH monomer on dissolution, the model system TFE$_{50}$/NB—F—OH$_x$/NB-di-F—OH$_{(50-x)}$ was studied. Results of the study are shown in the Table and Figure. This data shows that the addition of the NB-di-F—OH can increase the solubility of this system by a factor of $10^5$ and that one can use an appropriate ratio of NB—F—OH to NB-di-F—OH to tune the dissolution rate to any value between 0.01 nm/sec and 1000 nm/sec.

TABLE

Dissolution Rates of NB-di-F-OH Polymers

| Polymer | Rate (nm/sec) |
|---|---|
| TFE/NB-di-F-OH 50/50 | 1013* |
| TFE/NB-F-OH/NB-di-F-OH 50/22.5/27.5 | 7.5 |
| TFE/NB-F-OH/NB-di-F-OH 50/35/15 | 0.12 |
| TFE/NB-F-OH 50/50 | 0.01 |

*Extrapolated rate

Example 39

Synthesis of a TFE/NB—F—OH/NB-di-F—OH/TCN—(CO$_2$-t-Bu)(CO$_2$-t-Bu)/HAdA Pentapolymer A metal pressure vessel of approximate 270 mL capacity was charged with 50.75 g NB—F—OH, 17.01 g NB-di-F—OH, 11.2 g TCN—(CO$_2$-t-Bu)(CO$_2$-t-Bu) (prepared as known in the art by cycloaddition of di-tert-butyl-fumerate with quadracyclane), 1.11 g HAdA and 30 mL Solkane® 365 mfc. The vessel was closed, cooled to about −15° C., and pressured to 400 psi with nitrogen and vented several times. The reactor contents were heated to 50° C. TFE was added to a pressure of 340 psi and a pressure regulator was set to maintain the pressure at 340 psi throughout the polymerization by adding TFE as required. A solution of 2.66 g Perkadox®16N dissolved in 30 mL methyl acetate and diluted to 100 mL with Solkane® 365 mfc was pumped into the reactor at a rate of 2.0 mL/minute for 6 minutes, and then at a rate of 0.1 mL/minute for 8 hours. At the same time, a solution prepared by diluting 42.05 g NB—F—OH, 14.58 g NB-di-F—OH, 9.60 g TCN—($CO_2$-t-Bu)($CO_2$-t-Bu) and 9.99 g HAdA to 100 mL with Solkane® 365 mfc was pumped into the reactor at 0.10 mL/min for 12 hr. After 16 hours of reaction time, the vessel was cooled to room temperature and vented to 1 atmosphere. The recovered polymer solution was added slowly to an excess of hexane while stirring. The precipitate was filtered, washed with hexane and air-dried. The resulting solid was dissolved in a mixture of THF and Solkane® 365 mfc, and added slowly to excess hexane. The precipitate was filtered, washed with hexane and dried in a vacuum oven overnight to give 31.5 g of white polymer. GPC: Mn=7600; Mw=13800; Mw/Mn=1.82. $^{13}C$ NMR analysis showed the polymer composition to be 27% TFE, 31% NB—F—OH, 7% NB-di-F—OH, 9% TCN—($CO_2$-t-Bu)($CO_2$-t-Bu) and 26% HAdA. Anal. Found: C, 51.65; H, 5.12; F, 28.11.

Example 40

Synthesis of a TFE/NB-di-F—OH/2HEtA/HAdA Tetrapolymer

A metal pressure vessel of approximate 270 mL capacity was charged with 79.7 g NB-di-F—OH, 1.25 g 2HEtA, 5.59 g HAdA, 28.8 g THF and 25 mL methyl acetate. The vessel was closed, cooled to about −15° C., and pressured to 400 psi with nitrogen and vented several times. The reactor contents were heated to 50° C. TFE was added to a pressure of 240 psi and a pressure regulator was set to maintain the pressure at 240 psi throughout the polymerization by adding TFE as required. A solution of 6.4 g Perkadox®16N diluted to 100 mL with methyl acetate was pumped into the reactor at a rate of 2.0 mL/minute for 6 minutes, and then at a rate of 0.1 mL/minute for 8 hours. At the same time, a solution prepared by diluting 33.05 g NB-di-F—OH, 4.59 g 2HEtA and 20.52 g HAdA to 100 mL with methyl acetate was pumped into the reactor at 0.10 mL/min for 12 hr. After 16 hours of reaction time, the vessel was cooled to room temperature and vented to 1 atmosphere. The recovered polymer solution was added slowly to an excess of heptane while stirring. The precipitate was filtered, washed with heptane and air-dried. The resulting solid was dissolved in a mixture of THF and Solkane® 365 mfc, and added slowly to excess heptane. The precipitate was filtered, washed with heptane and dried in a vacuum oven overnight to give 107.98 g of white polymer. GPC: Mn=3900; Mw=6600; Mw/Mn=1.72. Anal. Found: C, 46.42; H, 4.78; F, 31.61.

Example 41

Synthesis of a TFE/TCN-(F2)(F2)/NB-di-F—OH/t-BuAc tetrapolymer

A metal pressure vessel of approximate 270 mL capacity was charged with 36.86 g TCN—(F2)(F2) (prepared as known in the art by cycloaddition of norbornadiene with TFE), 23.33 g NB-di-F—OH, 1.28 g t-BuAc and 25 mL Solkane® 365 mfc. The vessel was closed, cooled to about −15° C., and pressured to 400 psi with nitrogen and vented several times. The reactor contents were heated to 50° C. TFE was added to a pressure of 320 psi and a pressure regulator was set to maintain the pressure at 320 psi throughout the polymerization by adding TFE as required. A solution of 4.5 g Perkadox®16N dissolved in 40 mL methyl acetate and diluted to 100 mL with Solkane® 365 mfc was pumped into the reactor at a rate of 2.0 mL/min for 6 min, and then at a rate of 0.1 mL/minute for 8 hr. At the same time, a solution prepared by diluting 28.8 g TCN-(F2)(F2), 18.23 g NB-di-F—OH, and 8.00 g t-BuAc to 100 mL with Solkane® 365 mfc was pumped into the reactor at 0.10 mL/min for 12 hr. After 16 hr of reaction time, the vessel was cooled to room temperature and vented to 1 atmosphere. The recovered polymer solution was added slowly to an excess of hexane while stirring. The precipitate was filtered, washed with hexane and air-dried. The resulting solid was dissolved in a mixture of THF and Solkane® 365 mfc, and added slowly to excess hexane. The precipitate was filtered, washed with hexane and dried in a vacuum oven overnight to give 36.2 g of white polymer. GPC: $M_n$=8800; $M_w$=13000; $M_w/M_n$=1.49. $^{13}C$ NMR analysis showed the polymer composition to be 32% TFE, 26% TCN-(F2)(F2), 10% NB-di-F—OH, and 32% t-BuAc. Anal. Found: C, 47.82; H, 4.30; F, 37.60.

Example 42

Synthesis of a TFE/TCN-(F2)(F2)/NB-di-F—OH/TCN-(CO2-t-Bu)(CO2-t-Bu) Tetrapolymer A 400 mL pressure vessel was swept with nitrogen and charged with 36.86 g of TCN-(F2)(F2), 31.10 g of NB-di-F—OH, 20.48 g of TCN—($CO_2$-t-Bu)($CO_2$-t-Bu), 40 mL of Solkane® 365 mfc and 2.55 g of Perkadox®16N. The vessel was closed, cooled in dry ice, evacuated, and charged with 48 g of TFE. The vessel contents were heated to 50° C. and agitated for 18 hr as the internal pressure decreased from 350 psi to 331 psi. The vessel was cooled to room temperature and vented to one atmosphere. The vessel contents were added to excess hexane. The solid was filtered, washed with hexane, dissolved in THF and precipitated in hexane. This solid was filtered and dried in a vacuum oven at about 80° C. There was isolated 29.1 g of the white copolymer. GPC analysis: $M_n$=7200, $M_w$=10500, $M_w/M_n$=1.45. $^{13}C$ NMR analysis showed the polymer composition to be 48% TFE, 24% TCN—(F2)(F2), 10% NB-di-F—OH, and 18% TCN—($CO_2$-t-Bu)($CO_2$-t-Bu). Anal. Found: C, 49.29; H, 4.39; F, 35.04.

Example 43

Synthesis of a TFE/TCN-(F2)(F2)/NB-di-F—OH/t-BuAc/2HEtA Pentapolymer

A metal pressure vessel of approximate 270 mL capacity was charged with 27.36 g TCN-(F2)(F2) (prepared as known in the art by cycloaddition of norbornadiene with TFE), 46.17 g NB-di-F—OH, 1.15 g t-BuAc, 0.41 g 2HEtA and 25 mL Solkane® 365 mfc. The vessel was closed, cooled to about −15° C., and pressured to 400 psi with nitrogen and vented several times. The reactor contents were heated to 50° C. TFE was added to a pressure of 320 psi and a pressure regulator was set to maintain the pressure at 320 psi throughout the polymerization by adding TFE as required. A solution of 4.5 g Perkadox®16N dissolved in 40 mL methyl acetate and diluted to 100 mL with Solkane® 365 mfc was pumped into the reactor at a rate of 2.0 mL/min for 6 min, and then at a rate of 0.1 mL/min for 8 hr. At the same time, a solution prepared by diluting 21.6 g TCN-(F2)(F2), 36.45 g NB-di-F—OH, and 5.76 g t-BuAc and 2.03 g 2HEtA to 100 mL with Solkane®

365 mfc was pumped into the reactor at 0.10 mL/min for 12 hr. After 16 hr of reaction time, the vessel was cooled to room temperature and vented to 1 atmosphere. The recovered polymer solution was added slowly to an excess of heptane while stirring. The precipitate was filtered, washed with heptane and air-dried. The resulting solid was dissolved in a mixture of THF and Solkane® 365 mfc, and added slowly to excess heptane. The precipitate was filtered, washed with heptane and dried in a vacuum oven overnight to give 45.54 g of white polymer. GPC: $M_n$=7400; $M_w$=11900; $M_w/M_n$=1.61. Anal. Found: C, 45.61; H, 4.02; F, 37.09.

Example 44

Photoresist Prepared from a TFE/NB—F—OH/NB-di-F—OH/TCN—(CO$_2$-t-Bu)(CO$_2$-t-Bu)/HAdA Pentapolymer The following formulation was prepared and magnetically stirred overnight:

| Component | Wt. (gm) |
|---|---|
| TFE/NB-F-OH/NB-di-F-OH/TCN-(CO$_2$-t-Bu)(CO$_2$-t-Bu)/HAdA (27/31/7/9/26) polymer from Example 39 | 2.94 |
| 2-Heptanone | 20.46 |
| Solution of tetrabutylammonium lactate in 2-heptanone prepared as follows: 2.5 gm of aqueous tetrabutylammonium hydroxide (40%, Sigma-Aldrich Chemical Company) was dissolved in 97.5 gm ethyl lactate (Sigma-Aldrich Chemical Company). 13.0 gm of this solution was later dissolved in 13.0 gm of 2-heptanone. | 0.72 |
| 6.82 wt % solution of photoacid generator TPS-Nf dissolved in 2-heptanone that had been filtered through a 0.45 µm PTFE syringe filter. | 0.88 |

The wafer was prepared by applying a hexamethyldisilazane (HMDS) primer layer using a YES-3 vapor prime oven. A 100% HMDS adhesion promoter from Arch Chemical Co. was used. The oven was set to give a prime at 150° C. for 300 sec.

The sample was spin coated using a Brewer Science Inc. Model-100CB combination spin coater/hotplate on a 4 in. diameter Type "P", <100> orientation, silicon wafer. To prepare the coating, 2 ml of the above solution, after filtering through a 0.45 µm PTFE syringe filter, was deposited and spun at 2500 rpm for 60 sec, and then baked at 150° C. for 60 sec.

248 nm imaging was accomplished by exposing the coated wafer to light obtained by passing broadband UV light from an ORIEL Model-82421 Solar Simulator (1000 watt) through a 248 nm interference filter which passes about 30% of the energy at 248 nm. Exposure time was 15 seconds, providing an unattenuated dose of 20.5 mJ/cm$^2$. By using a mask with 18 positions of varying neutral optical density, a wide variety of exposure doses were generated. After exposure, the exposed wafer was baked at 135° C. for 60 sec.

The wafer was tray developed for 60 sec in aqueous 2.38 wt % tetramethylammonium hydroxide (TMAH) solution (LDD-26W, Rohm & Haas Electronics, Marlborough, Mass.). This test generated a positive image with a clearing dose of 3.6 mJ/cm$^2$.

What is claimed is:

1. A composition represented by Structure I

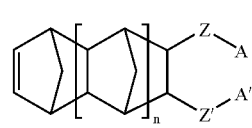

wherein n is 0, 1, or 2;

A and A' are independently $C(R_f)(R_f')OR^1$;

$R^1$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

Z and Z' are each —OCH$_2$—, or Z-A and Z'-A' taken together are

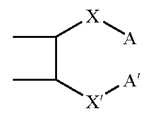

and X and X' are independently a direct bond, or a divalent group.

2. The composition of claim 1, wherein Z and Z' are each —O—CH$_2$— and n is 0.

3. The composition of claim 1, wherein Z-A and Z'-A' are taken together to form:

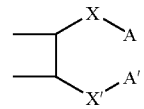

4. The composition of claim 3, wherein X and X' are —CH$_2$OCH$_2$—.

5. The composition of claim 1, wherein each of $R_f$ and $R_f'$ are CF$_3$.

6. The composition of claim 1, wherein $R^1$ is H or —CH$_2$OCH$_3$ or —CH$_2$OAd.

7. A polymer comprising a repeat unit derived from an unsaturated polycyclic compound represented by Structure II:

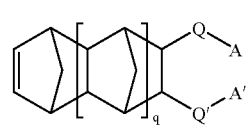

wherein q is 0, 1, or 2;

A and A' are independently $C(R_f)(R_f')OR^1$;

$R^1$ is hydrogen or an acid-labile protecting group;

$R_f$ and $R_f'$ are the same or different fluoroalkyl groups of 1 to 10 carbon atoms or taken together are $(CF_2)_m$ where m is 2 to 10;

Q and Q' are each a divalent group, a direct bond or Q-A and Q'-A' taken together are

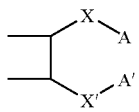

and X and X' are independently a direct bond, or a divalent group.

8. The polymer of claim 7, further comprising a repeat unit derived from an ethylenically unsaturated compound having at least one fluorine atom covalently attached to an ethylenically unsaturated carbon atom.

9. The polymer of claim 8, wherein the ethylenically unsaturated compound is a $C_2$-$C_{20}$ fluoro-olefin.

10. The polymer of claim 9, wherein the fluoro-olefin is selected from a group consisting of tetrafluoroethylene, hexafluoropropylene, chlorotrifluoroethylene, vinylidene fluoride, vinyl fluoride, perfluoro-(2,2-dimethyl-1,3-dioxole), perfluoro-(2-methylene-4-methyl-1,3-dioxolane), $CF_2=CFO(CF_2)_tCF=CF_2$, where t is 1 or 2, and $R_f''OCF=CF_2$ wherein $R_f''$ is a saturated fluoroalkyl group of from 1 to 10 carbon atoms.

11. The polymer of claim 10, wherein the fluoro-olefin is tetrafluoroethylene.

12. The polymer of claim 7, further comprising a repeat unit derived from an acrylate or a methacrylate monomer.

13. The polymer of claim 7, wherein $R^1$ is a protecting group.

14. The polymer of claim 7, wherein q is zero, and Q and Q' are each —$OCH_2$—, or Q-A and Q'-A' taken together are

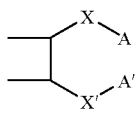

15. A photoresist composition comprising:
   a. a polymer comprising a repeat unit derived from an unsaturated polycyclic compound represented by Structure II:

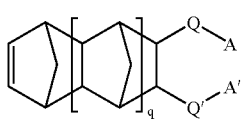

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Q and Q' are each a divalent group, a direct bond or Q-A and Q'-A' taken together are

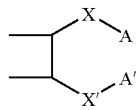

and X and X' are independently a direct bond, or a divalent group; and
   b. a photoactive component.

16. The composition of claim 15, further comprising a solvent.

17. A process for forming a coated substrate, comprising:
   A. coating a substrate with a mixture comprising:
      1. a polymer comprising a repeat unit derived from an unsaturated polycyclic compound represented by Structure II:

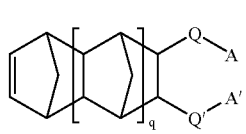

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;
Q and Q' are each a divalent group, a direct bond or Q-A and Q'-A' taken together are

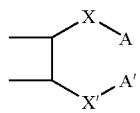

and X and X' are independently a direct bond, or a divalent group; and
      2. a photoactive component; and
      3. a solvent;
   B. evaporating the solvent.

18. A photoresist-coated substrate comprising:
   a. a substrate;
   b. a photoresist composition comprising:
      i. a polymer comprising a repeat unit derived from an unsaturated polycyclic compound represented by Structure II:

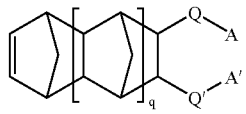

wherein q is 0, 1, or 2;
A and A' are independently $C(R_f)(R_f')OR^1$;
$R^1$ is hydrogen or an acid-labile protecting group;
$R_f$ and $R_f'$ are the same or different fluoroalkyl groups of 1 to 10 carbon atoms or taken together are $(CF_2)_m$ where m is 2 to 10;

Q and Q' are each a divalent group, a direct bond or Q-A and Q'-A' taken together are
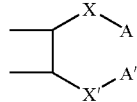
and X and X' are independently a direct bond, or a divalent group; and
ii. a photoactive component,
wherein the photoresist is coated on the substrate.
* * * * *